(12) United States Patent
Rasochova et al.

(10) Patent No.: US 11,364,214 B2
(45) Date of Patent: Jun. 21, 2022

(54) COMPOSITIONS AND METHODS FOR TREATING ECZEMA

(71) Applicant: Dermala Inc., San Diego, CA (US)

(72) Inventors: Lada Rasochova, Del Mar, CA (US); Michelle Kem, San Diego, CA (US)

(73) Assignee: Dermala, Inc., San Diego, CA (US)

( * ) Notice: Subject to any disclaimer, the term of this patent is extended or adjusted under 35 U.S.C. 154(b) by 0 days.

(21) Appl. No.: 16/302,639

(22) PCT Filed: May 18, 2017

(86) PCT No.: PCT/US2017/033347
§ 371 (c)(1),
(2) Date: Nov. 17, 2018

(87) PCT Pub. No.: WO2017/201297
PCT Pub. Date: Nov. 23, 2017

(65) Prior Publication Data
US 2019/0290605 A1    Sep. 26, 2019

Related U.S. Application Data

(60) Provisional application No. 62/338,344, filed on May 18, 2016.

(51) Int. Cl.
*A61K 31/19* (2006.01)
*A61P 17/00* (2006.01)
(Continued)

(52) U.S. Cl.
CPC ............ *A61K 31/19* (2013.01); *A61K 9/0014* (2013.01); *A61K 9/06* (2013.01); *A61K 31/194* (2013.01);
(Continued)

(58) Field of Classification Search
CPC ....... A61P 17/00; A61K 31/19; A61K 31/194; A61K 31/197; A61K 31/22; A61K 31/221;
(Continued)

(56) References Cited

U.S. PATENT DOCUMENTS

| 6,177,071 B1 * | 1/2001 | Lin ......................... A61K 8/066 424/78.03 |
| 2004/0253282 A1 * | 12/2004 | Sauermann ............ A61Q 19/08 424/401 |

(Continued)

FOREIGN PATENT DOCUMENTS

| KR | 20070042868 A * | 4/2007 |
| WO | WO 2012/084978 A1 | 6/2012 |
| WO | WO 2015/106175 A1 | 7/2015 |

*Primary Examiner* — Marcos L Sznaidman
*Assistant Examiner* — Rayna Rodriguez
(74) *Attorney, Agent, or Firm* — Torrey Pines Law Group, PC (57) ABSTRACT

Disclosed are compositions, methods of treatment using the compositions and methods of preparing the compositions for the treatment of eczema. The compositions may include propionic acid and/or non-steroidal esters of propionic acid. The compositions may further include a corticosteroid, immunomodulator, antibiotic, antibody, colloidal oatmeal, conditioned media prepared by bacterial fermentation, short chain fatty acids, picolinic acid, or emollient. The method of treatment may include analysis of the skin microbiome.

2 Claims, 4 Drawing Sheets

(51) Int. Cl.
| | |
|---|---|
| A61P 31/04 | (2006.01) |
| A61P 29/00 | (2006.01) |
| A61K 9/00 | (2006.01) |
| A61K 9/06 | (2006.01) |
| A61K 31/197 | (2006.01) |
| A61K 31/22 | (2006.01) |
| A61K 31/225 | (2006.01) |
| A61K 31/25 | (2006.01) |
| A61K 31/436 | (2006.01) |
| A61K 31/56 | (2006.01) |
| A61K 36/899 | (2006.01) |
| A61K 39/395 | (2006.01) |
| A61K 47/46 | (2006.01) |
| C07K 16/28 | (2006.01) |
| C07K 16/42 | (2006.01) |
| A61K 31/194 | (2006.01) |
| A61K 31/58 | (2006.01) |
| A61K 31/573 | (2006.01) |
| A61K 31/221 | (2006.01) |
| A61K 45/06 | (2006.01) |

(52) U.S. Cl.
CPC ............ *A61K 31/197* (2013.01); *A61K 31/22* (2013.01); *A61K 31/221* (2013.01); *A61K 31/225* (2013.01); *A61K 31/25* (2013.01); *A61K 31/436* (2013.01); *A61K 31/56* (2013.01); *A61K 31/573* (2013.01); *A61K 31/58* (2013.01); *A61K 36/899* (2013.01); *A61K 39/3955* (2013.01); *A61K 39/39566* (2013.01); *A61K 45/06* (2013.01); *A61K 47/46* (2013.01); *A61P 17/00* (2018.01); *A61P 29/00* (2018.01); *A61P 31/04* (2018.01); *C07K 16/2866* (2013.01); *C07K 16/4291* (2013.01); *C07K 2317/21* (2013.01); *C07K 2317/24* (2013.01)

(58) Field of Classification Search
CPC .... A61K 31/223; A61K 31/23; A61K 31/436; A61K 31/56; A61K 31/573; A61K 31/58; A61K 9/0014; A61K 9/06; A61K 36/899; A61K 39/3955; A61K 39/39566; A61K 45/06; A61K 47/46; C07K 16/2866; C07K 16/4291; C07K 2317/21; C07K 2317/24

See application file for complete search history.

(56) References Cited

U.S. PATENT DOCUMENTS

| | | |
|---|---|---|
| 2008/0279900 A1 | 11/2008 | Longo et al. |
| 2011/0104240 A1* | 5/2011 | Jones ................ A23B 4/16 424/443 |
| 2014/0243299 A1 | 8/2014 | Gurge et al. |
| 2014/0323584 A1 | 10/2014 | Cornmell et al. |
| 2015/0306230 A1 | 10/2015 | Combs et al. |

* cited by examiner

COMPOSITIONS AND METHODS FOR TREATING ECZEMA

CROSS-REFERENCE TO RELATED APPLICATIONS

This application claims priority from U.S. Provisional Application Ser. No. 62/338,344 filed on May 18, 2016, which is incorporated herein by reference in its entirety.

STATEMENT REGARDING FEDERALLY SPONSORED RESEARCH OR DEVELOPMENT

Not Applicable.

FIELD

The present invention is related to compositions and methods for the treatment of eczema, and, in particular, to topical compositions and methods based upon pharmaceutically and cosmetically acceptable preparations of propionic acid and derivatives thereof.

INTRODUCTION

Eczema (also referred to as atopic dermatitis or AD) predominantly occurs in children in developed countries and is continuing to increase in prevalence among children of low-income nations. The disease is also seen in many adults and follows a relapsing course. AD patients show signs of psychological and psychosocial distress to discomfort and embarrassment or anger regarding their appearance, and patients over 16 years of age showed significantly lower scores on social functioning and mental health than the general population. Up to 60% of children with AD report sleep disturbance due to itching, increasing to 83% during exacerbation, which typically affects the sleep of other household members.

Disease onset also comes with a significant financial burden for patients and families with an economic impact of almost 1 billion US dollars each year in the USA. The market opportunity is significant with therapeutic sales in the nine major markets—the US, France Germany, Italy, Spain, UK, Japan, China and India—are expected to reach $5.6 billion by 2022 at a Compounded Annual Growth Rate (CAGR) of 3.8%.

The disease pathogenesis of AD is believed to be due to a combination of environmental and genetic factors resulting in compromised skin barrier function, inflammation and the appearance of erythema and papules. Up to 80-100% of patients suffering from AD are colonized with *S. aureus* compared to only about 5-30% of control patients. During AD flare-ups, the loss of microbiome diversity towards an overgrowth of *S. aureus* correlates with disease severity. *S. aureus* strains isolated from AD lesions have been shown to produce a variety of toxins and enzymes with aggressive cell-damaging and inflammation-inducing properties. *S. aureus* directly damages keratinocytes by adhering to cells and forming transmembrane pores through the secretion of staphylococcal toxin ultimately leading to the breakdown of cellular ATP metabolism. *S. aureus* superantigens elicit the production of IgE antibodies, which levels correlate with disease severity.

Treatments for AD, which reduce the bacterial load, include the administration of oral antibiotics, topical corticosteroids, toxin neutralizing agents and dilute bleach bath, although, studies have shown that *S. aureus* colonization can rapidly reoccur following termination of treatment, and it is recommended that long-term treatments are used to reduce the occurrence of AD associated flare-ups. Treatment with anti-staphylococcal antibiotics in conjunction with topical corticosteroids demonstrated better clinical improvement than treatment with topical corticosteroids alone suggesting treatments aimed at reducing the bacterial load are effective. Long-term treatments with antibiotics, however, are not advised due to the propensity of *S. aureus* strains to form antibiotic resistance. Methicillin-resistant *S. aureus* strains have developed an elaborate set of defenses against commonly used antibiotics and resistant *S. aureus* strains have been isolated from AD lesions. The prolonged use of topical corticosteroids is also not recommended due to side-effects, and a survey of 200 dermatology outpatients with AD showed that 72.5% of parents worried about applying topical corticosteroids onto their children and 24% of them admitted non-compliance due to these concerns.

Thus there is a need for new treatments for AD that can decrease the toxic and inflammatory effects induced by *S. aureus* colonization with minimal side effects and a low propensity for developing resistance, reduced level of disease recurrence and longer disease-free periods.

SUMMARY

Accordingly, the inventors herein have succeeded in devising new compositions and methods of treatment for AD based upon based upon pharmaceutically and cosmetically acceptable preparations of propionic acid and derivatives thereof.

Thus, in various embodiments, the present invention includes a topical composition for the treatment of AD. The composition includes propionic acid or a non-steroidal ester of propionic acid in a pharmaceutically acceptable topical preparation.

In various other embodiments, propionic acid is prepared by fermentation of *P. acnes*. The fermentation product of *P. acnes*, called conditioned media, is used in the formulation of a topical treatment for atopic dermatitis.

In various other embodiments, propionic acid or a non-steroidal ester of propionic acid is prepared by chemical synthesis.

In various other embodiments, the present invention includes a method of treating AD. The method includes administering to a subject in need thereof, a topical composition comprising propionic acid or a non-steroidal ester of propionic acid in a pharmaceutically acceptable topical preparation.

In still other embodiments, the present invention includes a method of preparing a topical formulation for treating AD, the method comprising combining propionic acid or a non-steroidal ester of propionic acid with a carrier substance in a pharmaceutically acceptable topical preparation.

In various of the embodiments above, the composition may include propionic acid in a pharmaceutically acceptable topical preparation. The propionic acid may be present in the composition in an amount suitable for delivering to the skin at least 1 mM propionic acid.

In various of the embodiments above, the composition may include the non-steroidal derivative of propionic acid, 2-(2-propionyloxyethoxy)ethylester (PA-DEG-PA) in a pharmaceutically acceptable topical preparation. The PA-DEG-PA may be present in the composition in an amount suitable for delivering to the skin at least 1 mM-DEG-PA.

In various of the embodiments above, the composition may include the non-steroidal derivative of propionic acid, (1R,2S,5R)-2-Isopropyl-5-methylcyclohexyl propionate (M-PA) in a pharmaceutically acceptable topical preparation. The M-PA may be present in the composition in an amount suitable for delivering to the skin at least 1 mM M-PA.

In various of the embodiments above, the composition may include the non-steroidal derivative of propionic acid $C_{12}H_{20}O_6$, glyceryl tripropionate-tripropionin (tri-PA) in a pharmaceutically acceptable topical preparation. The tri-PA may be present in the composition in an amount suitable for delivering to the skin at least 1 mM tri-PA.

In various of the embodiments above, the composition may include the non-steroidal derivative of propionic acid 2-[2-(propionyloxy)ethoxy]ethyl propionate (di-PA) in a pharmaceutically acceptable topical preparation. The di-PA may be present in the composition in an amount suitable for delivering to the skin at least 1 mM di-PA. In various of the embodiments above, the composition may include the non-steroidal derivative of propionic acid propionylcholineiodide (ch-PA) in a pharmaceutically acceptable topical preparation. The ch-PA may be present in the composition in an amount suitable for delivering to the skin at least 1 mM ch-PA. In various of the embodiments above, the composition may include the non-steroidal derivative of propionic acid propionyl-L-carnitine (ca-PA) in a pharmaceutically acceptable topical preparation. The ca-PA may be present in the composition in an amount suitable for delivering to the skin at least 1 mM ca-PA.

In various of the embodiments above, the composition may include the non-steroidal derivative of propionic acid that is an ester of glycerol and propionic acid (PA-glycerol-PA) in a pharmaceutically acceptable topical preparation. The PA-glycerol-PA may be present in the composition in an amount suitable for delivering to the skin at least 1 mM PA-glycerol-PA.

In various embodiments, the composition may further include a corticosteroid. The corticosteroid may be any one or more of clobetasol propionate, diflorasone diacetate, halobetasol propionate, betamethasone, dipropionate, desoximetasone, diflorasone diacetate, fluocinonide, halcinonide, mometasone furoate, triamcinolone acetonide, clocortolone pivalate, desoximetasone, fluocinolone acetonide, flurandrenolide, fluticasone propionate, mometasone furoate, triamcinolone acetonide, hydrocortisone, hydrocortisone acetate, fluocinolone acetonide, hydrocortisone probutate, hydrocortisone valerate, prednicarbate and desonide.

In various embodiments, the composition may further include an antibiotic. The antibiotic may be anti-staphylococcal antibiotic such as muciprocin, clindamycin, rifampin, doxycycline, or a quinolone.

In various embodiments, the composition may further include an immunomodulator. The immunomodulator may be a calcineurin inhibitor such as tacrolimus or pimecrolimus.

In various embodiments, the composition may further include an antibody. The antibody may be a monoclonal antibody that blocks IgE function such as Omalizumab or Dupilumab that blocks the IL-4 receptor alpha subunit.

In various embodiments, the composition may further include colloidal oatmeal.

In various embodiments, the composition may further include other short chain fatty acids or their derivatives. The short chain fatty acid may be succinic acid or butyric acid. Short chain fatty acids or their derivatives should be in a concentration that will deliver a dose to the skin that is below MIC for P. acnes.

In various embodiments, the composition may further include picolinic acid or its derivatives.

In various embodiments, the composition may further include succinic acid. The succinic acid should be in concentrations that is below MIC for P. acnes.

In various embodiments the composition may further include conditioned media prepared by fermentation of P. acnes.

In various embodiments, the composition may further include an emollient. The emollient may be white pertrolatum, coconut oil, and other moisture-retaining compounds.

These and other features, aspects and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

DETAILED DESCRIPTION

The present invention is directed to new compositions, methods of treatment and methods of formulation based upon compositions for AD. The compositions are based upon pharmaceutically acceptable preparations of propionic acid and derivatives thereof.

It has been shown previously by Shu et al. (Shu, M. et al. Fermentation of Propionibacterium acnes, a Commensal Bacterium in the Human Skin Microbiome, as Skin Probiotics against Methicillin-Resistant Staphylococcus aureus, PLoS One. 2013; 8(2):e55380, pp. 1-11) and Wang et al. (Wang, Y. et al., Propionic acid and its esterified derivative suppress the growth of methicillin resistant Staphylococcus aureus USA300, Beneficial Microbes, 2014; 5(2): 161-168) that propionic acid and fermentation products of P. acnes inhibit growth of S. aureus. However, it has not been known that these compounds can be used for the treatment of eczema, reduce itching associated with eczema and eczema symptoms in skin patches and disease recurrence. Additionally, propionic acid can be cosmetically unacceptable due to a strong odor and therefore not suitable for continuous use. Formulations containing odor-free derivatives of propionic acid were identified that showed properties suitable for skincare applications for the treatment of eczema. Additionally, combination products of propionic acid and derivatives thereof with other APIs (active pharmaceutical ingredients) that are currently used for the treatment of eczema and eczema-like diseases were identified and used for the treatment of eczema that provide synergistic effects and significantly improved unexpected properties compared to the API alone including being significantly faster-acting, having less side effects, controlling S. aureus overgrowth as well as inflammation and resulting in less frequent disease recurrence thus managing the symptoms of eczema significantly more efficiently. Combination products were also identified that are suitable for use in children due to reduced side effects that are suitable for long term use.

Definitions

As used herein, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

As used herein, the term "about" is intended to refer to a range of values above and below a stated value such as for example, values encompassing 10% below up to 10% above a stated value.

The term "and/or" is intended to mean either or both of two recited elements.

"Active pharmaceutical ingredient" ("API") refers to a substance, in particular an antimicrobial or anti-inflammatory agent, in a pharmaceutical composition that is delivered for a desired effect.

As used herein, the term "combination" with respect to active agents refers to a composition of two or more active agents, in particular, antimicrobial and anti-inflammatory agents. In the present invention, a combination of active agents may include propionic acid derivative of propionic acid. The compositions may further include P. acne-derived conditioned media, a corticosteroid, immunomodulator, antibiotic, antibody, short chain fatty acid (succinic acid or butyric acid), picolinic acid, colloidal oatmeal, and/or emollient. A steroid refers to an organic compound with four rings, A, B, C and D arranged in the specific configuration as shown below:

An example of a steroid compound having the four rings, A, B, C and D is shown below with IUPAC-approved ring lettering and atom numbering:

A non-steroidal compound refers to a compound that lacks the typical steroid four ring system above.

A corticosteroid refers to any of a group of steroid hormones produced in the adrenal cortex or made synthetically. There are two kinds: glucocorticoids and mineralocorticoids of which glucocorticoids have been used in treating various skin diseases involving inflammation. Unless otherwise indicated herein, the term corticosteroid is intended to refer to glucocorticoids when used in connection with compositions and methods for treating various skin diseases.

Such corticosteroids that are glucocorticoids include, but are not limited to clobetasol propionate, diflorasone diacetate, halobetasol propionate, betamethasone, dipropionate, desoximetasone, diflorasone diacetate, fluocinonide, halcinonide, mometasone furoate, triamcinolone acetonide, clocortolone pivalate, desoximetasone, fluocinolone acetonide, flurandrenolide, fluticasone propionate, mometasone furoate, triamcinolone acetonide, hydrocortisone, hydrocortisone acetate, fluocinolone acetonide, hydrocortisone probutate, hydrocortisone valerate, prednicarbate, desonide and combinations thereof.

An antibiotic refers to antibiotic creams and ointments such as anti-staphylococcal antibiotic including muciprocin, clindamycin, rifampin, doxycycline, or a quinolone.

An immunomodulator refers to Tacrolimus which is an immunomodulator that acts as a calcineurin inhibitor. Tacrolimus is available in 2 strengths, 0.1% for adults and 0.03% for children, although 0.1% preparation is routinely used in children. Tacrolimus is an ointment and is indicated for moderate-to-severe AD. It is indicated for children older than 2 years. Pimecrolimus 1% is also an immunomodulator and calcineurin inhibitor. Pimecrolimus is produced in a cream base for use twice a day; it is indicated for mild AD in persons older than 2 years and is particularly useful on the face. A 2006 black box warning has been issued in the United States based on research that has shown an increase in malignancy in association with the calcineurin inhibitors. These agents are also much more expensive than corticosteroids and should only be used as second-line therapy. Pimecrolimus cream has been marketed as Elidel and tacrolimus ointment and Protopic.

An antibody refers to Omalizumab which is a monoclonal antibody that blocks IgE function, Dupilumab which is another monoclonal antibody that blocks the IL-4 receptor alpha subunit, which is required for both IL-4 and IL-13 signaling, and other monoclonal antibodies that are involved with IgE function blocking.

Short chain fatty acids refers to succinic acid, butyric acid or their derivatives. These short chain fatty acids should be used in concentrations to deliver dose to the skin that is below P. acnes MIC. These short chain fatty acids should provide anti-inflammatory effects and not antimicrobial effect (because they are present in a concentration below MIC).

Colloidal oatmeal refers to substance produced by finely grinding the oat and boiling it to extract the colloidal material. Colloidal oatmeal is used as a skin protectant. Its use as a skin protectant is regulated by the U.S. Food and Drug Administration (FDA) according to the Over-The-Counter Final Monograph for Skin Protectant Drug Products issued in June 2003.

An emollient refers to substances that soften and moisturize the skin. Emollients/moisturizers work by forming an oily layer on the top of the skin that traps water in the skin. Petrolatum, lanolin, mineral oil, coconut oil and dimethicone are common emollients. Emollients can also contain humectants, including glycerin, lecithin, and propylene glycol that draw water into the outer layer of skin. Many products also have ingredients that soften skin (allantoin). Other moisturizers include white petrolatum, Aquaphor, Atopiclair, Mimyx, and other emollients composed of ceramides, cholesterol and lipids naturally found in the top layer of the skin. The active ingredient should be applied before or together with the emollient.

Conditioned media refers to fermentation products produced during *Propionibacterium acnes* (*P. acnes*) fermentation and secreted into the media.

Reference herein to an API including, but not limited to propionic acid, a derivative of propionic acid and/or a corticosteroid, antibiotic, immunomodulator, antibody, conditioned media, succinic acid, propionic acid, picolinic acid, colloidal oatmeal, emollient is intended to include pharmaceutically acceptable solvates, salts, hydrates or hydrated salts, their optical isomers, racemates, diastereomers, enantiomers or the polymorphic crystalline structures of the compounds.

The term "pharmaceutical composition" or 'pharmaceutical preparation" refers to a composition that combines one or more API's with a pharmaceutically acceptable carrier such that the composition is suitable for therapeutic use in vitro, in vivo or ex vivo.

As used herein, the term "pharmaceutically acceptable carrier" encompasses any suitable pharmaceutical carriers, such as a phosphate buffered saline solution, water, and emulsions, such as an oil/water or water/oil emulsion, various types of wetting agents and the like. The compositions also can include stabilizers and preservatives. Examples of carriers, stabilizers and adjuvants, can be found in Remington: The Science and Practice of Pharmacy, Lippincott Williams & Wilkins, Twenty-First edition (May 19, 2005).

As used herein, the term "cosmetically acceptable" encompasses any formulation that is acceptable for topical use free of offensive odors, unnatural colors or unacceptable side effects.

Unless otherwise indicated, concentrations are given as mass weight percentages, i.e. w/w %. Mass weight percentages (w/w %) for combination formulations are calculated as follows:

$$\text{mass \% } a = \text{mass}(a) \div (\text{mass}(a) + \text{mass}(b) + \text{mass}(c) + \ldots) \times 100 \text{ (w/w \%)}.$$

Compositions

The present invention includes compositions, treatment methods and formulation methods based upon compositions that may include propionic acid and a derivative of propionic acid. The compositions may also include *P. acnes* conditioned media, a corticosteroid, and/or antibiotic, immunomodulator, antibody, colloidal oatmeal, emollient, short chain fatty acids, succinic acid, butyric acid, and/or picolinic acid.

In various embodiments, the composition may include propionic acid in an amount that delivers from about 1 to about 1,000 mM propionic acid to the skin. Such compositions may include propionic acid in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of propionic acid in the composition may be about 0.1, about 0.2, about 0.5, about 0.75, about 1, about 2, about 3, about 4, about 5, about 6, about 7, about 8, about 9 or about 10 w/w %. The propionic acid may further be combined with one or more API's and a carrier system.

In various embodiments, the composition may include a derivative of propionic acid that is a non-steroidal ester of propionic acid. In various embodiments, the non-steroidal ester may be 2-(2-propionyloxyethoxy)ethylester (PA-DEG-PA) in a pharmaceutically acceptable topical preparation. The PA-DEG-PA may be present in the composition in an amount that delivers from about 1 to about 1,000 mM PA-DEG-PA to the skin. Such compositions may include PA-DEG-PA in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of PA-DEG-PA in the composition may be about 0.1, about 0.2, about 0.5, about 0.75, about 1, about 2, about 3, about 4, about 5, about 6, about 7, about 8, about 9 or about 10 w/w %. The PA-DEG-PA may further be combined with one or more API's which may include a corticosteroid, antibiotic, immunomodulator, antibody, colloidal oatmeal, short chain fatty acid (succinic acid or butyric acid), picolinic acid, emollient, *P. acnes* conditioned media and a carrier system. In various embodiments, the composition may include the non-steroidal ester (1R,2S,5R)-2-isopropyl-5-methylcyclohexyl propionate (M-PA) in a pharmaceutically acceptable topical preparation. The M-PA may be present in the composition in an amount that delivers from about 1 to about 1,000 mM M-PA to the skin. Such compositions may include M-PA in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of M-PA in the composition may be about 0.1, about 0.2, about 0.5, about 0.75, about 1, about 2, about 3, about 4, about 5, about 6, about 7, about 8, about 9 or about 10 w/w %. The M-PA may further be combined with one or more API's which may include a corticosteroid, antibiotic, immunomodulator, antibody, colloidal oatmeal, short chain fatty acid (succinic acid or butyric acid), picolinic acid, emollient, *P. acnes* conditioned media and a carrier system. In various embodiments, the composition may include the non-steroidal ester of glycerol and propionic acid (PA-glycerol-PA) in a pharmaceutically acceptable topical preparation. The PA-glycerol-PA may be present in the composition in an amount that delivers from about 1 to about 1,000 mM PA-glycerol-PA to the skin. Such compositions may include PA-glycerol-PA in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of PA-glycerol-PA in the composition may be about 0.1, about 0.2, about 0.5, about 0.75, about 1, about 2, about 3, about 4, about 5, about 6, about 7, about 8, about 9 or about 10 w/w %. The PA-glycerol-PA may further be combined with one or more API's which may include a corticosteroid, antibiotic, immunomodulator, antibody, colloidal oatmeal, short chain fatty acid (succinic acid or butyric acid), picolinic acid, emollient, *P. acnes* conditioned media and a carrier system.

In various of the embodiments above, the composition may include the non-steroidal derivative of propionic acid $C_{12}H_{20}O_6$, glyceryl tripropionate-tripropionin (tri-PA) in a pharmaceutically acceptable topical preparation. The tri-PA may be present in the composition in an amount that delivers from about 1 to about 1,000 mM tri-PA to the skin. Such compositions may include tri-PA in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of tri-PA in the composition may be about 0.1, about 0.2, about 0.5, about 0.75, about 1, about 2, about 3, about 4, about 5, about 6, about 7, about 8, about 9 or about 10 w/w %. The tri-PA may further be combined with one or more API's which may include a corticosteroid, antibiotic, immunomodulator, antibody, colloidal oatmeal, short chain fatty acid (succinic acid or butyric acid), picolinic acid, emollient, P. acnes conditioned media and a carrier system.

In various of the embodiments above, the composition may include the non-steroidal derivative of propionic acid 2-[2-(propionyloxy)ethoxy]ethyl propionate (di-PA) in a pharmaceutically acceptable topical preparation. The di-PA may be present in the composition in an amount that delivers from about 1 to about 1,000 mM di-PA to the skin. Such compositions may include di-PA in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of di-PA in the composition may be about 0.1, about 0.2, about 0.5, about 0.75, about 1, about 2, about 3, about 4, about 5, about 6, about 7, about 8, about 9 or about 10 w/w %. The di-PA may further be combined with one or more API's which may include a corticosteroid, antibiotic, immunomodulator, antibody, colloidal oatmeal, short chain fatty acid (succinic acid or butyric acid), picolinic acid, emollient, P. acnes conditioned media and a carrier system.

In various of the embodiments above, the composition may include the non-steroidal derivative of propionic acid propionylcholineiodide (ch-PA) in a pharmaceutically acceptable topical preparation. The ch-PA may be present in the composition in an amount that delivers from about 1 to about 1,000 mM ch-PA to the skin. Such compositions may include ch-PA in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of ch-PA in the composition may be about 0.1, about 0.2, about 0.5, about 0.75, about 1, about 2, about 3, about 4, about 5, about 6, about 7, about 8, about 9 or about 10 w/w %. The ch-PA may further be combined with one or more API's which may include a corticosteroid, antibiotic, immunomodulator, antibody, colloidal oatmeal, short chain fatty acid (succinic acid or butyric acid), picolinic acid, emollient, P. acnes conditioned media and a carrier system.

In various of the embodiments above, the composition may include the non-steroidal derivative of propionic acid propionyl-L-carnitine (ca-PA) in a pharmaceutically acceptable topical preparation. The ca-PA may be present in the composition in an amount that delivers from about 1 to about 1,000 mM ca-PA to the skin. Such compositions may include ca-PA in an amount of from about 0.01 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of ca-PA in the composition may be about 0.1, about 0.2, about 0.5, about 0.75, about 1, about 2, about 3, about 4, about 5, about 6, about 7, about 8, about 9 or about 10 w/w %. The ca-PA may further be combined with one or more API's which may include a corticosteroid, antibiotic, immunomodulator, antibody, colloidal oatmeal, short chain fatty acid (succinic acid or butyric acid), picolinic acid, emollient, P. acnes conditioned media and a carrier system.

The compositions of the present invention may be incorporated into a pharmaceutically acceptable carrier system which may include creams, ointments, gels, lotions, solutions, cleansing solutions, and the like. Pharmaceutically acceptable carriers may include a surfactant such as an anionic surfactant, a cationic surfactant, a zwitterionic surfactant or a nonionic surfactant. Pharmaceutically acceptable carrier systems may also contain ingredients that include, but are not limited to, saline, aqueous electrolyte solutions, ethanol, dimethyl sulfoxide, dimethyl isosorbide, isopropyl myristate, lauryl lactate, diisopropyl adipate, sodium lauryl sulfoacetate; ionic and nonionic osmotic agents such as sodium chloride, potassium chloride, glycerol, propylene glycol and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; compounds such as lecithin, phospholipids; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using preservatives, including, but are not limited to, benzalkonium chloride, ethylene diamine tetra-acetic acid and its salts, benzethonium chloride, chlorhexidine, chlorobutanol, methylparaben, thimerosal, and phenylethyl alcohol, natural preservatives such as grapefruit seed extract, or may be formulated as a non-preserved formulation for either single or multiple use.

Methods of Treatment

The methods of treatment of the present invention are useful for the treatment of skin diseases including AD flare-ups that are associated with a skin microbiome dysbiosis, including an overgrowth of *S. aureus, Corynebacterium* and/or other microbes in the skin microbiome and a decrease of *P. acnes* and/or other microbes in the skin microbiome. Treatment of AD may include determining the skin microbiome profile of a subject, administering to a subject a composition that includes a one or more API's, and monitoring the response and disease state including prevention of flare-ups by monitoring the skin microbiome profile of a subject.

The compositions of the present invention can be administered at a variety of intervals. In some instances, administration may be once a day. In other instances, administration can be less or more frequently, such as 1, 2, 3, or 4 times a day, 1 time every 2 days, or once a week.

The treatment methods may be monitored by following any of the pathogenic aspects of AD including skin microbiome profiling including determining the levels and ratios of *S. aureus, Corynebacterium* and *P. acnes* in the skin microbiome, genomic and histologic profiling of lesional biomarkers including markers of epidermal hyperplasia, markers of cellular infiltrates and terminal differentiation as well as the measuring of immune markers of inflammatory mediators (See, for example, Mansouri, Y. et al., Immune Pathways in Eczema, and Definition of Biomarkers through Broad and Targeted Therapeutics, *J. Clin Med.* 2015 May; 4(5): 858-873).

Formulation Methods

Formulation methods known in the art may be used to prepare the compositions of the present invention. For example, a one-batch formulation method may be used in which the components of the pharmaceutical formulation are combined in a single container and the components may be added to the container simultaneously or consecutively.

EXAMPLES

Example 1. Preparation of Bacterial Cultures and Conditioned Media

Preparation of S. aureus (ATCC 29213): A 10 ml culture of S. aureus was prepared in cation-adjusted Mueller Hinton II Broth (CA-MHB) and grown at 37° C., 215 RPM overnight. The overnight culture was subcultured in fresh CA-MHB and grown at 37° C., 215 RPM until an optical density at 600 nm (OD600 nm) of 1.0 was reached. This inoculum preparation was used for all experiments.

Preparation of P. acnes (ATCC 6919) conditioned media: A P. acnes inoculum (5 ml) was prepared in Reinforced Clostridial Media (RCM) and grown anaerobically at 37° C. in a Gas-Pak (BD) for 48 hours. This culture was subcultured into 5 ml aliquots of fresh RCM and anaerobically grown at 37° C. for 15 days with or without 1% glycerol. P. acnes in RCM without glycerol, RCM with glycerol only, and RCM only were used as controls. The cells were pelleted by centrifugation (12,000×g, 2 mins) and the supernatants were removed and filtered through a 0.22 µm filter for sterilization. The filtered supernatants were aliquoted and stored at −80° C. until use.

Example 2. Minimal Inhibitory Concentration Assay and Time-Kill Assay

The minimal inhibitory concentration (MIC): MIC of P. acnes fermentation extracts, propionic acid (PA), and tripropionin (tri-PA) against S. aureus were determined according to the microbroth dilution method from the Clinical Laboratory Standards Institute (CLSI) document M100-S22. S. aureus was cultured as described above, pelleted by centrifugation, washed with PBS and resuspended in PBS to a concentration of $10^7$ CFU/ml. Two-fold serial dilutions of the P. acnes glycerol fermentation extract (90 µl) or propionic acid (0-100 mM) were added to wells in a 96-well plate followed by 10 µl of the prepared S. aureus inoculum. The MIC of tripropionin was evaluated with and without the presence of 0.2 mg/ml porcine liver esterase (Sigma #E3019-20KU) and the assay was prepared as described for PA. All assays with PA and tri-PA were performed in the presence of 10% DMSO. P. acnes glycerol fermentation extract, PA or tri-PA without S. aureus and TSB broth with S. aureus only were used for negative and positive controls, respectively. Plates were incubated under aerobic conditions for 16 hours at 37° C. Following incubation, each well was resuspended by pipetting and the optical density at 600 nm (OD600) was determined on a plate reader. The MIC value was defined as the first well showing ≥90% reduction in growth compared to controls.

Time-kill assay: A time-kill assay was performed to monitor the bactericidal activity of propionic acid (PA). An inoculum of S. aureus was prepared as described above and combined with PA at concentrations corresponding to 1×, 2× and 4× the MIC of PA (15 mM) in TSB broth. A final concentration of $10^5$ CFU/ml of S. aureus was used. Assays were performed in 100 µl volumes in 96-well plates and incubated at 37° C. in a sealed bag to prevent evaporation. At various time points (0, 1, 7, and 24 hours) 10 µl of each sample was removed and diluted 1:10 to $1:10^4$ in sterile PBS and 20 µl of each dilution was spotted in triplicate on a TSB agar plates. Bacterial growth was determined by counting CFUs. The bactericidal properties of PA and tri-PA against S. aureus were also evaluated in the presence of an esterase. Each drug was used at a concentration 4× the MIC value and 0.2 mg/ml porcine liver esterase. The assay was setup and evaluated as described above. Samples were analyzed after 0, 1, 5, and 24 hours.

Example 3. MIC Assay of P. acnes Conditioned Media Against S. aureus

Figure 1:
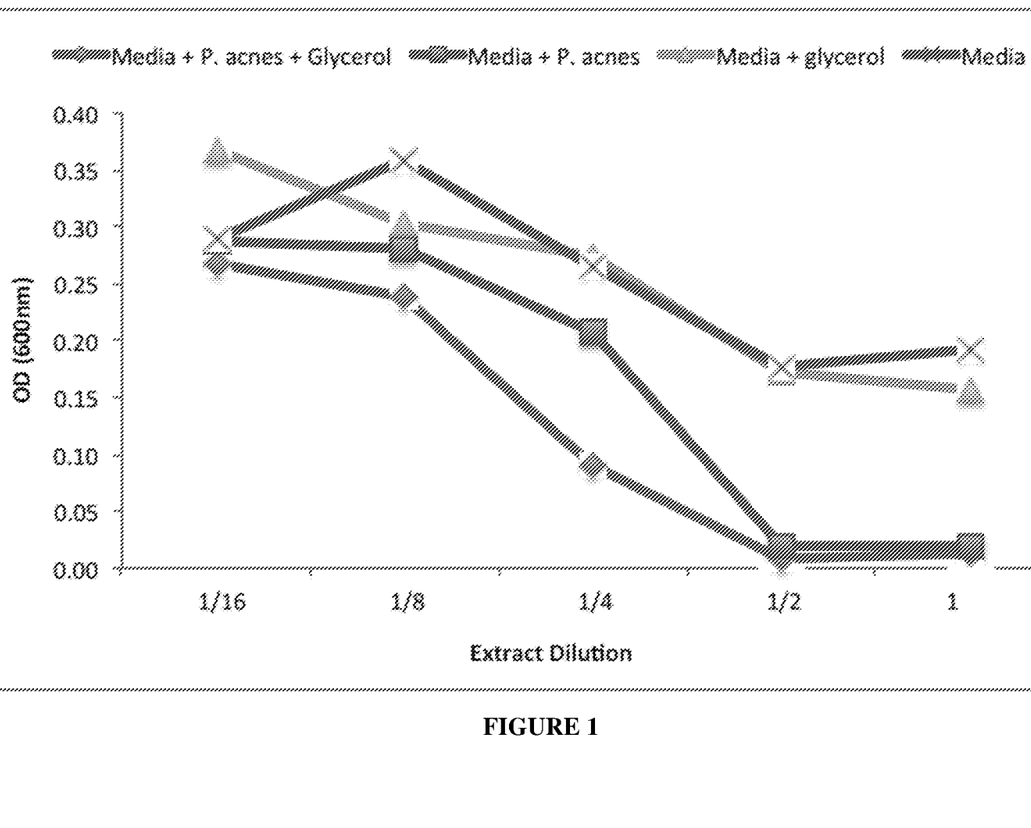
FIG. 1 shows MIC assay of P. acnes conditioned media against S. aureus.

S. aureus was incubated with two-fold serial dilutions of P. acnes conditioned media to monitor the growth inhibitory properties. FIG. 1 shows the decrease in growth of S. aureus with higher concentrations of the P. acnes conditioned media. The P. acnes conditioned media (blue and red) inhibited the growth of S. aureus when the broth is diluted 1:2 whereas the media with glycerol control (green) and media only control (purple) did not inhibit S. aureus growth. The P. acnes conditioned media without glycerol inhibited S. aureus growth at a 1:2 dilution which suggested that the RCM broth contained a substrate for P. acnes fermentation (red).

Example 4. Bactericidal Properties of Propionic Acid Against S. aureus

Figure 2:
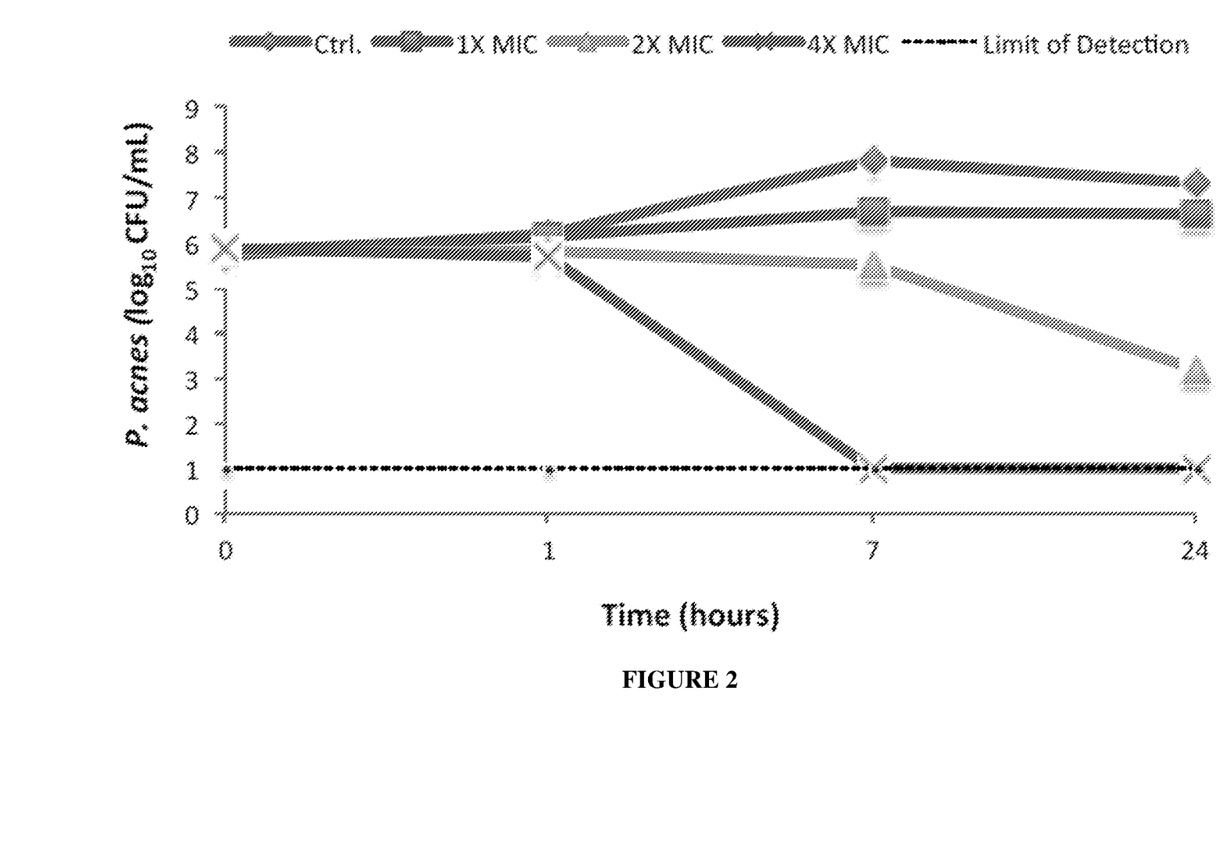
FIG. 2 shows evaluation of the bactericidal properties of PA against S. aureus using the time-kill assay.

The bactericidal properties of PA against S. aureus were evaluated using the time-kill assay. Concentrations of PA at 1×, 2× and 4× the MIC (15 mM) were tested against S. aureus and samples were measured after 0, 1, 7, and 24 hours. FIG. 2 shows that at 4× the MIC, PA is bactericidal against S. aureus after 7 hours. After 7 hours, PA is shown to be bactericidal against S. aureus at 4× the MIC.

Example 5. Growth Inhibitory Properties of Tripropionin Against S. aureus

Figure 3:
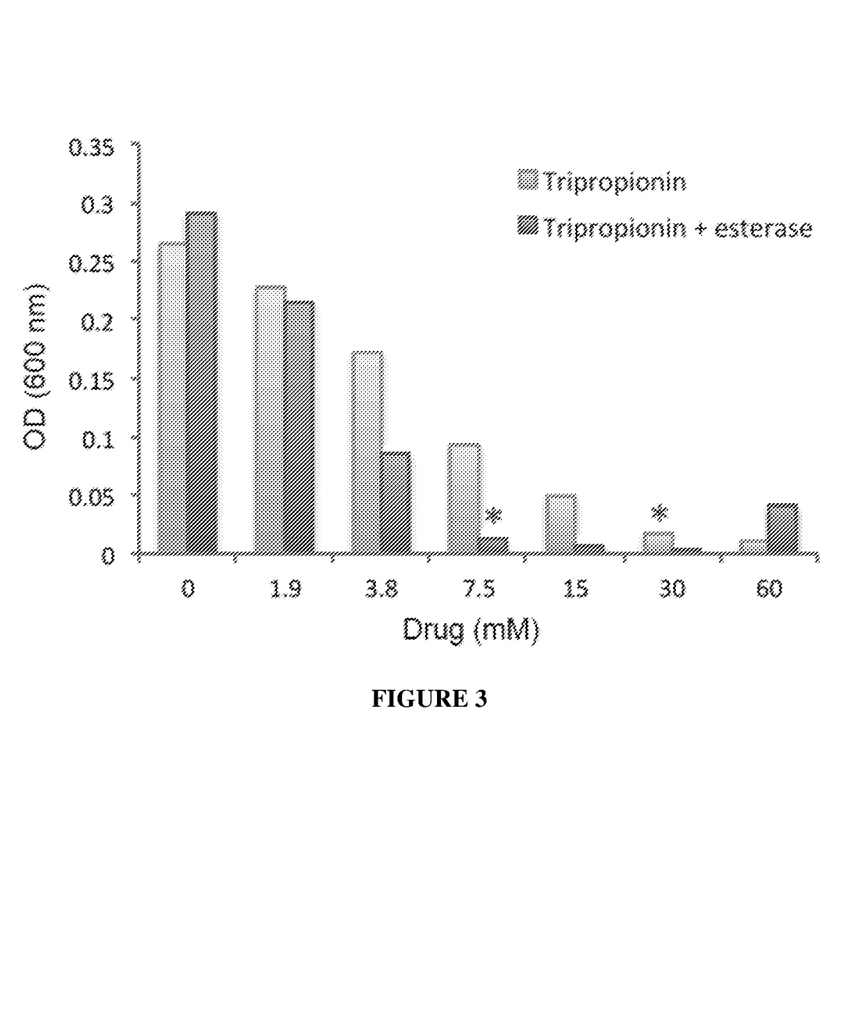
FIG. 3 shows MIC values for the growth inhibition of S. aureus by tripropionin with or without the addition of an esterase.

The growth inhibitory properties of tripropionin (tri-PA, T-PA) against S. aureus were evaluated in the presence of an esterase. FIG. 3 shows that the MIC value of tri-PA against S. aureus was 30 mM when an esterase was not added (green). However, when an esterase was added to the reaction (purple), the MIC value decreased to 7.5 mM. This shows that tri-PA inhibited the growth of S. aureus and its growth inhibitory properties were increased in the presence of an esterase.

Figure 4:
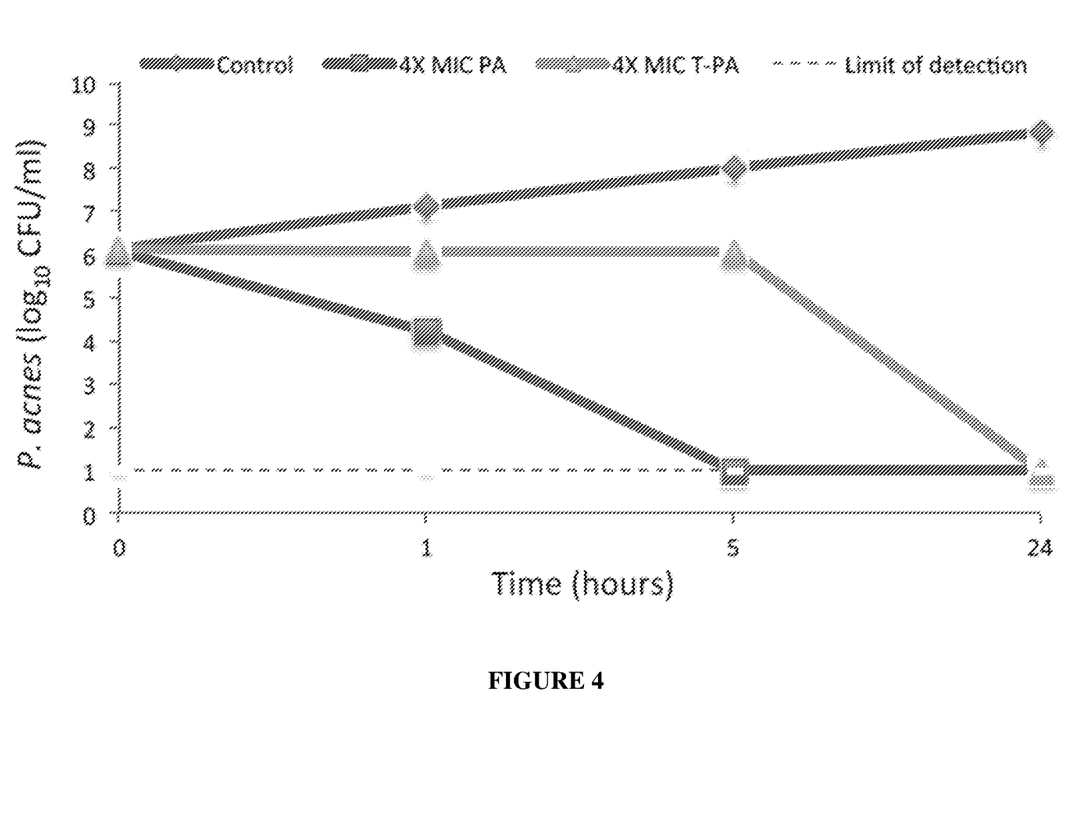
FIG. 4 shows PA and TPA time kill assay in the presence of an esterase.

Example 6. Bactericidal Properties of PA and Tri-PA in the Presence of an Esterase The bactericidal properties of PA and tri-PA against S. aureus were compared in the presence of an esterase. Both compounds were tested at a concentration 4× the determined MIC and compared to a growth control. FIG. 4 shows PA and tri-PA time kill assay in the presence of an esterase. PA showed complete killing of S. aureus after 5 hours and tri-PA was able to completely kill S. aureus after 24 hours.

Example 7: Formulation of Tripropionin into a Topical Cream and Testing

A 5% tripropionin topical cream was formulated using a 50/50 shea butter and coconut oil base with or without 1% colloidal oatmeal. The Shea butter and coconut oil were slowly heated at a low temperature until melted. The mixture was cooled to about 30° C. and triproionin and colloidal oatmeal were added. The mixture was then whipped with a mixer until a homogenous, light solid formed.

Example 8: Testing of the Topical Cream in Human Subjects for the Treatment of Eczema The topical cream containing 5% tripropionin with or without 1% colloidal oatmeal and prepared in the Example 7 was tested in human subjects with eczema. The subjects applied the cream two times per day or whenever needed to reduce itching. The following values were recorded prior and post application: general skin health, itching, appearance of eczema patches (presence of raised skin, oozing/weeping, bleeding, skin softness/smoothness), and side effects. Results showed that after application of the topical formulation containing 5% tripropionin with or without 1% colloidal oatmeal no negative side effects were observed. The subjects used using various topical products for eczema treatment but experienced constant itching in eczema patches that persisted despite prior to using other products. After application of the cream containing tripropionic (+/−colloidal oatmeal), the itching was reduced by at least 80% after application of the cream for 2 days. In 50% of patches, the itching stopped completely after use. There was significant improvement in the general skin health and the skin in eczema patches became much smoother and softer and the appearance of eczema patches became less visible. The oozing/weeping of the skin stopped and any previous bleeding stopped and the patches started healing. The cosmetic acceptability was scored as excellent.

Example 9: Testing of Antimicrobial Properties of PA and PA Derivatives

This example compares PA, PA-DEG-PA, M-PA, tri-PA, di-PA, ch-PA, ca-PA, PA-glycerol-PA and other derivatives for antimicrobial properties.

The anti-*S. aureus* activity of PA and PA-derivatives are compared by determining the minimal inhibitory concentration (MIC) and minimal bactericidal concentration (MBC) of each compound in the presence/absence of keratinocyte lysates. Briefly, 2-fold serial dilutions of each compound (0-100 mM) are made in 96-well plates and incubated with equal volumes of keratinocyte lysates and *S. aureus*. Toxin producing *S. aureus* strain 8325-4 and 5 clinical isolates of *S. aureus* strains obtained from the skin of AD patients are used in this experiment. Following 48 hours of incubation at 37° C., the samples are resuspended by pipetting and the optical density at 600 nm (OD600 nm) are analyzed. The MIC value are defined as the concentration of drug in the first well displaying ≥90% reduction in growth. The MBC values are determined as follows. Briefly, the samples from the MIC assay are diluted 1:10 to 1:$10^6$ and each dilution are spread on a TSB agar plate for CFU counting. The MBC value are defined as the first concentration displaying ≥3 $\log_{10}$ drop in CFU/ml. Appropriate negative controls are included, including PBS and appropriate vehicles used to resuspend PA or PA derivatives (+/−keratinocyte lysates).

The antimicrobial properties of PA and PA derivatives are compared. PA and PA derivatives show antimicrobial properties against *S. aureus* including bactericidal effects both in the presence and absence of keratinocyte lysates. The anti-*S. aureus* activity is higher in the presence of keratinocyte lysates. Tri-PA was selected for formulation into a cream and further testing in humans.

Example 10: Anti-Inflammatory Properties of PA and PA Derivatives

This example compares PA, PA-DEG-PA, M-PA, tri-PA, di-PA, ch-PA, ca-PA, PA-glycerol-PA and other derivatives for anti-inflammatory properties and determines if the compounds can protect keratinocytes from the *S. aureus* induced toxicity in vitro.

*S. aureus* colonized on AD lesions exacerbate AD symptoms through the secretion of proteins, toxins and superantigens. *S. aureus* superantigens (*S. aureus* enterotoxin B (SEB), *S. aureus* enterotoxin A (SEA) and toxic shock syndrome toxin-1 (TSST-1)) are produced by 57%-65% of *S. aureus* strains isolated from AD lesions and induce an inflammatory response in keratinocytes through the synthesis and release of TNF-α. Certain *S. aureus* strains also produce Staphylococcal protein A (SpA), which induces a TNF-α mediated immune response as well. *S. aureus* directly damages keratinocytes by adhering to the cells and the releasing the lysis-inducing toxin, α-toxin.

Attenuation of inflammatory responses induced by Staphylococcal protein A, SpA by PA and PA derivatives is measured as follows: The spontaneously immortalized human keratinocyte cell line, HaCaT (Addexbio Technologies), is used to measure the reduction of TNF-α release following stimulation with SpA (Sigma) by PA and PA derivatives. Briefly, 5×105 cells/ml are plated in 24-well plates and incubated for 24 hours. The cells are treated with SpA (10 µg/mL) for 0-24 hours at 37° C. PA or PA derivatives are added to the cells in varying concentrations (0-100 mM) 10 min, 1, 6, 12 and 24 hours prior to the addition of SpA. This measures if PA or derivatives can prevent SpA-induced TNF-α production. Varying concentrations of PA or PA derivative are also added concurrently with SpA or 10 min, 1, 6, 12 and 24 hours after the addition of SpA. This measures if PA or derivatives can assuage the SpA-induced inflammatory response. Controls, including incubating HaCaT cells with PBS (negative control), and incubating HaCaT cells with PA or PA derivative alone are included in testing. As a positive control, LPS, a known stimulator of keratinocytes, is used to induce an inflammatory response in HaCaT cells. Culture supernatants are removed at various time points (0-24 hours) to monitor release of TNF-α using a commercially available ELISA kit. The anti-inflammatory properties of PA or PA derivatives are determined. PA and PA derivatives cause reduction in inflammatory responses when applied prior and/or post stimulation.

Example 11: Reduction of Cytotoxic Effects of *S. aureus* on Keratinocytes by PA and PA Derivatives These experiments determine that PA or PA derivative decrease the cytotoxic effect of *S. aureus* on keratinocytes. The analysis is performed as follows: Primary epidermal keratinocyte cultures NHEK (ATCC® PCS-200-011) are used in these experiments. Briefly, *S. aureus* strain 8325-4 ($10^6$ CFU/ml) are grown aerobically in nutrient broth, centrifuged and washed twice with 0.85% NaCl followed by resuspention in keratinocyte basal medium. The resuspended bacteria are then added to NHEK cells (5×$10^3$ cells/$cm^3$) in 24-well plates. Varying concentrations of PA or PA derivatives (0-100 mM) are added to the NHEK cells prior to, concurrently or following incubation with *S. aureus* and the ability of each drug to protect keratinocytes from the cytotoxic effects of *S. aureus* is determined. PBS and appropriate vehicles (used to resuspend PA or PA derivative)

are used as negative control. Cell viability is determined by MTT/ESTA (3-[4,5-dimethylthiazol-2-yl]-2,5-diphenyl-tetrazolium bromide/eluted stain assay) after 1, 3, 6, 12 and 24 hours of incubation. To determine if PA and PA derivatives protect keratinocytes by inhibiting the growth of *S. aureus* in cell culture, the viability of *S. aureus* is measured. Briefly, *S. aureus* (100 μl, $10^6$ cells/ml) is added to confluent NHEK cells in the presence or absence of PA or PA derivative. In separate experiments, the supernatant is removed after 2, 4, 8, 16, and 24 hours and centrifuged to pellet the free bacteria. Since *S. aureus* adheres to keratinocytes, the NHEK cells are also trypsinized and incubated in 0.25% triton x-100 in PBS to lyse the cells. The lysed keratinocytes are combined with the pelleted supernatant and serial dilutions (1:10 to $1:10^6$) are plated on supplemented *Brucella* broth agar to count the total number of viable *S. aureus* cells. PA and PA derivatives show protective properties towards keratinocytes and reduce cytotoxis effects of *S aureus* on keratinocytes. PA or PA derivative exhibit concentration-dependent attenuation in TNF-α release following keratinocyte stimulation by SpA. In addition to SpA, other *S. aureus* superantigens, such as staphylococcal enterotoxin B (SEB) and toxic shock syndrome toxin-1 (TSST-1), that elicit TNF-α production in keratinocytes, can be used for TNF-α induction and PA and PA derivatives evaluation. PA or PA derivatives are added prior to, during, or post incubation with SEB or TSST-1 to monitor changes in TNF-α production. PA derivative with a smaller MW (<500 Da) will be preferentially used to increase cell membrane penetration properties.

The tri-PA candidate displaying both the anti-*S. aureus* and anti-inflammatory properties was used for formulation development and cream containing tri-PA with or without colloidal oatmeal was used for the treatment of eczema.

Example 12: Combination Products for the Treatment of Eczema

PA derivatives that exhibit antimicrobial properties but do not exhibit sufficient anti-inflammatory properties are used for the treatment of eczema in combination with corticosteroids. The rationale for combining PA or PA derivative with corticosteroids is to decrease the concentration of corticosteroids needed to treat AD lesions resulting in a treatment with fewer side effects, restoring a healthier, more diverse microbiome, restoring *P. acnes* in the microbiome, preventing *S. aureus* overgrowth. Products with lower concentration of corticosteroids are suitable for a long-term treatment approach. The combination product provide significant improvement of efficacy due to synergistic effects of anti-inflammatory, antimicrobial (provided by PA and/or PA derivatives) and skin repair properties of the product that is critical for eczema treatment.

Example 13: Combination Products for the Treatment of Eczema

PA and PA derivatives are also formulated in combination with antibiotics. The rationale for combining PA or PA derivatives with antibiotics is to decrease the concentration of antibiotics needed to treat *S. aureus* overgrowth and *S. aureus*-associated infections in AD subjects resulting in treatment with fewer side effects and less risk of developing resistance. Resistance prevention is a significant benefit that is provided by PA or PA derivative component in the formulation. Avoidance and/or lower doses of antibiotics restores a healthier, more diverse microbiome while increasing *P. acnes* in the microbiome and preventing *S. aureus* overgrowth. This makes the product suitable for a long-term treatment approach. In addition, the combination product provide synergies and significant improvement of efficacy due to anti-inflammatory, skin healing and antimicrobial properties of the product.

PA and PA derivatives are also formulated in combination with immunomodulators including tacrolimus or pimecrolimus. The rationale for combining PA or PA derivatives with immunomodulators is to decrease the concentration of immunomodulators needed to treat AD resulting in treatment with fewer side effects that restores a healthier, more diverse microbiome, increases *P. acnes* in the microbiome and prevents *S. aureus* overgrowth, and is suitable for a long-term treatment approach. In addition, PA or PA derivatives improve the efficacy of tacrolimus or pimecrolimus when tacrolimus or pimecrolimus is used in recommended strength of 0.1% tacrolimus for adults and 0.03% tactrolimus for children or 1% pimecrolimus. The combination product provide significant improvement of efficacy due to synergistic effects of anti-inflammatory, antimicrobial (provided by PA and/or PA derivatives) and skin repair properties of the product that is critical for eczema treatment.

PA and PA derivatives are also formulated in combination with antibodies, such as monoclonal antibodies Omalizuma, Dupilumab and other monoclonal antibodies that block IgE function. The rationale for combining PA or PA derivatives with antibodies is to decrease the concentration of antibodies needed to treat AD resulting in a treatment with fewer side effects, less cost, and restoring a healthier, more diverse microbiome, increasing *P. acnes* in the microbiome and preventing *S. aureus* overgrowth, and a treatment suitable for a long-term use. The combination product provide significant improvement of efficacy due to synergistic effects of anti-inflammatory, antimicrobial and skin repair properties of the combination product that is critical for eczema treatment.

PA and PA derivatives are also formulated in combination with short chain fatty acids including succinic acid and butyric acid and their derivatives. The rationale for combining PA-based compounds with short chain fatty acid (succinic acid or butyric acid) is to significantly increase anti-inflammatory effects of the composition. The combination product provide significant improvement of efficacy due to synergistic effects of anti-inflammatory, antimicrobial and skin repair properties of the combination product that is critical for eczema treatment.

PA and PA derivatives are also formulated in combination with emollients such as white petrolate. The rationale for combining PA or PA derivatives with emollients is to restore dysfunctional epidermal barrier, combat xerosis and transepidermal water loss. The PA or PA detivative are applied before or at the same time as the emollient.

Example 14: Combination Products for the Treatment of Eczema

The rationale for combing PA-based compounds with corticosteroids, antibiotics, immunomodulators, antibodies, colloidal oatmeal or other APIs is to improve the efficacy of the treatment and potentially decrease the concentration of APIs needed to treat AD resulting in a treatment with fewer side effects that may be better suited for a long-term treatment. The combination product provide significant improvement of efficacy due to synergistic effects of anti-inflammatory, antimicrobial and skin repair properties of the combination product that is critical for eczema treatment.

The rationale for combining PA-based compounds with short chain fatty acid (succinic acid or butyric acid) is to increase anti-inflammatory effects of the composition.

The rationale for combining PA-based compounds with *P. acnes* conditioned media is to increase anti-inflammatory and anti-*S. aureus* effects of the composition.

The rationale for combining PA-based compounds with picolinic acid is to increase anti-*S. aureus* effects of the composition.

The PA-based combination candidate are formulated into a suitable format (lotion, cream, gel, or ointment) and used for the treatment of eczema.

Example 15. Method for Treating and Monitoring Eczema

This example describes methods for treating and monitoring eczema that incorporate skin microbiome analysis. It has been shown that AD subjects have skin microbiome dysbiosis which includes increase in *Staphylococcus* and *Corynebacterium* bacteria on their skin. At the same time, inflammation increases and the quality of the skin's protective barrier deteriorates. Proliferation of *Staphylococcus* and *Corynebacterium* bacteria is associated with reduction of *Propionibacterium* and other beneficial bacteria. AD flare-ups are also associated with *Staphylococcus* and *Corynebacterium* bacteria increase. The correlation between the bacterial overgrowth and eczema including inflammation and the condition of the skin's protective barrier. A method of treatment of eczema includes the following steps:
1) Obtaining a sample of skin microbiome.
2) Analysis of skin microbiome
3) Determining the levels of microbiome dysbiosis by determining the levels of microbes such as *Staphylococcus, Corynebacterium* and *Propionibacterium* bacteria and comparing them to levels of *Staphylococcus, Corynebacterium* and *Propionibacterium* bacteria in healthy skin.
4) Deciding on the treatment regimen, which may include applying a treatment containing PA or PA derivatives.
5) Applying the treatment and monitoring symptoms.
6) Monitoring treatment effectiveness by monitoring the skin microbiome changes.
7) Changing the treatment if the levels of *Staphylococcus, Corynebacterium* and *Propionibacterium* remain unchanged.
8) Predicting AD flare-up timing by monitoring the skin microbiome dysbiosis.
9) Restarting treatment if levels *Staphylococcus, Corynebacterium* and *Propionibacterium* are becoming dysbiotic.
10) Incorporating microbiome history into the AD subject treatment record.

Microbiome sampling may include skin swabs. Microbiome analysis may include 16S RNA sequencing, PCR, or ELISA-based approaches. Microbiome analysis may be performed by specialized clinics, laboratories or by subjects themselves.

As various changes could be made in the above methods and compositions without departing from the scope of the invention, it is intended that all matter contained in the above description shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicant reserves the right to challenge the accuracy and pertinency of the cited references.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention. Specifically intended to be within the scope of the present invention, and incorporated herein by reference in its entirety, is the following publications:

Shu, M. et al. Fermentation of *Propionibacterium acnes*, a Commensal Bacterium in the Human Skin Microbiome, as Skin Probiotics against Methicillin-Resistant *Staphylococcus aureus*, PLoS One. 2013; 8(2):e55380, pp. 1-11.

Wang, Y. et al., Propionic acid and its esterified derivative suppress the growth of methicillin resistant *Staphylococcus aureus* USA300, Beneficial Microbes, 2014; 5(2): 161-168.

What is claimed is:

1. A method of treating atopic dermatitis (AD), the method comprising administering to a subject in need thereof, a composition consisting of tripropionin (Tri-PA) in a pharmaceutically acceptable topical preparation.

2. The method of claim 1, wherein the Tri-PA is present in the composition in an amount from about 0.5 w/w % to about 10 w/w %.

* * * * *